United States Patent [19]

Kossoff

[11] 4,070,905
[45] Jan. 31, 1978

[54] ULTRASONIC BEAM SCANNING

[75] Inventor: George Kossoff, Northbridge, Australia

[73] Assignee: The Commonwealth of Australia, Phillip, Australia

[21] Appl. No.: 731,697

[22] Filed: Oct. 12, 1976

[30] Foreign Application Priority Data

Oct. 13, 1975 Australia .............................. 3548/75

[51] Int. Cl.² ........................................... G01N 29/00
[52] U.S. Cl. ....................................... 73/614; 73/629; 128/2 V
[58] Field of Search ............... 73/67.7, 67.8 R, 67.8 S, 73/67.9; 128/2 V

[56] References Cited

U.S. PATENT DOCUMENTS

| 3,415,110 | 12/1968 | Cowan | 73/67.8 S |
| 3,789,833 | 2/1974 | Bom | 73/67.7 X |
| 3,888,238 | 6/1975 | Meindl et al. | 73/67.7 X |
| 3,911,730 | 10/1975 | Niklas | 73/67.7 |
| 3,919,683 | 11/1975 | Itamura et al. | 73/67.8 S X |

Primary Examiner—James J. Gill

[57] ABSTRACT

Apparatus for the ultrasonic examination of an object comprises:
a linear transducer array for directing pulses of ultrasonic energy along a plurality of beams into the object and receiving echoes of the pulses reflected along the beams by acoustic impedance discontinuities within the object, the transducer array comprising a plurality of adjacent transducer elements; and either means for sequentially activating different groups of adjacent transducer elements within the array to direct a pulse of ultrasonic energy along a beam into the object and receive echoes reflected along the beam in each of a plurality of angular directions in a single plane; or means for activating different groups of adjacent transducer elements within the array in turn so that each group directs pulses of ultrasonic energy into the object and receives echoes reflected along beams in a plurality of angular directions in a single plane.

6 Claims, 4 Drawing Figures

ULTRASONIC BEAM SCANNING

This invention relates to the technique of ultrasonic echoscopy of objects and in particular to an extension of known techniques of ultrasonic echoscopy to provide more useful information concerning the examined objects. It is particularly, but not solely, directed to the more effective acquisition of data in medical diagnosis utilising this technique.

Ultrasonic echoscopy provides information about an examined object which may be displayed in the form of an ultrasonic echogram. Such an echogram consists of a display of acoustic impedance discontinuities or reflecting surfaces in the object. It is obtained by directing a short pulse of ultrasonic energy, typically in the 1–30 MHz frequency range, along a line called the beam axis into the examined object where any acoustic impedance discontinuities in the object reflect and return some of the energy along the same beam axis in the form of an echo. This echo is received, converted into an electric signal and displayed as an echogram on a cathode ray oscilloscope, a film, a chart or the like.

The echogram may constitute either a one dimensional or a two dimensional representation and in both cases the information is contained in the position and magnitude of the echo displayed. In a one dimensional display, the position along a base line is used to indicate the distance to the reflecting surface whilst the magnitude of the echo is displayed, for example, as a deflection of the base line ("A" mode) or as an intensity change ("B" mode). In a two dimensional display, the position along a base line is used to indicate the distance to the reflecting surface as in a one dimensional display, and the direction of the base line is used to represent the direction of propagation of the acoustic energy which is the beam axis. The two dimensional display is obtained by changing this direction of propagation of the acoustic energy and by instituting a similar but not necessarily identical movement of the base line of the display. The magnitude of the echo is displayed as for a one dimensional display; for example, as a deflection of the base line or as an intensity change.

The technique of ultrasonic echoscopy is used in medical diagnosis to obtain information about the anatomy of patients. The application of this technique is now widely investigated and is described, for example, by D. E. Robinson in Proceeding of the Institution of Radio and Electronics Engineers Australia, Vol. 31, No. 11, pages 385 - 392, November, 1970: "The Application of Ultrasound in Medical Diagnosis". As pointed out in this article, ultrasonic echoscopy may be used to produce displays resembling anatomical cross-sections which have proved clinically useful when the desired information concerns physical dimensions, shapes of organs or structures or the like. Ultrasonic echography has proved of particular value as a diagnostic aid in the abdomen and pregnant uterus, eye, breast, brain, lung, kidney, liver and heart, these being areas of soft tissue with little bone and air. In general, the technique is considered to complement other techniques to provide a more complete picture of the patients condition, however particularly in pregnancies, ultrasonic echoscopy may be useful in place of X-rays where the latter may not give sufficient information or may be dangerous. In medical use, a pulse of ultrasonic energy is transmitted into a patient in a known direction and echoes are received from reflecting surfaces within the body. The time delay between a transmitted pulse and the received echo depends on the distance from the transmitter to the reflecting surface and the distance information so obtained may be displayed in a suitable way for interpretation and clinical use as a one dimensional range reading or as a two dimensional cross section as previously described.

This known system suffers from a disadvantage due to the time required to obtain a cross-section. The cross-section is made up of a multiplicity of lines of information corresponding to each beam axis position at which a pulse was transmitted and echoes received. The time required to obtain each line of information is fixed by the depth of the tissues of interest and the velocity of propagation of sound in the tissues to be examined. For a particular area of interest neither of these parameters is under the control of the operator and they form a basic limitation on the time required to obtain an echogram. By way of an example, consider the visualisation of the heart, with a resolution of one millimeter over an examination area of 10 centimeters square with a maximum depth below the surface of 15 centimeters. For each cross-sectional picture, 100 lines or beam axis positions are required and the minimum time required for each position is 200 microseconds, making a minimum time of 20 milliseconds. Thus the absolute maximum rate of obtaining complete pictures is 50 times per second, which is insufficient for some diagnostic situations.

It is well known in the art to provide a plurality of transducer elements to provide a plurality of parallel lines of sight, one for each transducer element. This approach suffers from the disadvantage that the size of each transducer element and therefore the resolution of each element is fixed by the spacing between lines on the final echogram. It is taught by Wilcox in U.S. Pat. No. 3,881,466 to use a plurality of transducer elements to form each ultrasonic beam, thus breaking the link between the line spacing and the resolution. It is also known, for example in U.S. Pat. No. 3,166,731 to Joy and U.S. Pat. No. 3,086,195 to Halliday, to apply time delays to signals associated with the various transducer elements forming a beam to cause the beam to be steered at an angle to the transducer array and also to achieve a focussing action within the plane of scan. It is further known (Kossoff U.S. Pat. No. 3,936,791) to place a cylindrical lens on the front of the transducer array to improve resolution at right angles to the scan plane. Finally, it is known (Kossoff U.S. Pat. No. 3,939,707) to measure blood flow along the ultrasonic line of sight by measuring the frequency shift of the returned echoes and to combine this information with information obtained from the B mode ultrasonic echogram of the area to measure blood flow absolutely.

It is a primary objective of the present invention to use a single multi-element transducer array to provide compound scans particularly of moving structures.

According to a first aspect of this invention, there is provided apparatus for the ultrasonic examination of an object comprising:

a linear transducer array for directing pulses of ultrasonic energy along a plurality of beams into the said object and receiving echoes of said pulses reflected along said beams by acoustic impedance discontinuities within the object, said transducer array comprising a plurality of adjacent transducer elements; and means for activating different groups of adjacent transducer elements within said array in turn so that each group directs pulses of ultrasonic energy into the object and receives echoes reflected along beams in a plurality of angular directions in a single plane.

In another aspect, this invention provides apparatus for the ultrasonic examination of an object comprising:

a linear transducer array for directing pulses of ultrasonic energy along a plurality of beams into the said object and receiving echoes of said pulses reflected along said beams by acoustic impedance discontinuities within the object, said transducer array comprising a plurality of adjacent transducer elements; and means for sequentially activating different groups of adjacent transducer elements within said array to direct a pulse of ultrasonic energy along a beam into the object and receive echoes reflected along the beam in each of a plurality of angular directions in a single plane.

This invention also extends to methods of ultrasonic examination of objects utilising the apparatus hereinbefore described.

In general the present invention provides means for examination of an object utilising a linear transducer array operated in a combined scan pattern. This combined scan can be provided either by the direct superposition of a linear and sector scan in a single frame or by providing lines of sight at different angles during consecutive frames and relying on the averaging properties of the eye to produce the compound scan image.

In yet another aspect, the apparatus of this invention may further include means to activate said linear transducer array to transmit pulses of ultrasonic energy into portion of said object along a beam in said plane and to determine the shift in frequency of echoes of said pulses caused by flow of liquid in said portion. In this aspect the linear array transducer is used to produce a real time B mode picture and concurrently the same or another part of the array is used to produce a line of sight for a pulsed Doppler beam for the measurement of blood flow.

This invention is illustrated in the accompanying drawings, which illustrate the invention by way of example, and in which:

FIG. 1 shows the well known structure of an ultrasonic linear array, in which the elements 1 are usually rectangular in shape and are arranged side-by-side in a line as shown. In accordance with this invention, this structure may be used in conjunction with known suitable electronic apparatus to form a sector scan pattern or a linear array pattern.

Figure 1:
FIG. 1 illustrates the arrangement of transducer elements in a linear transducer array which may be used in accordance with this invention.
Figure 2:
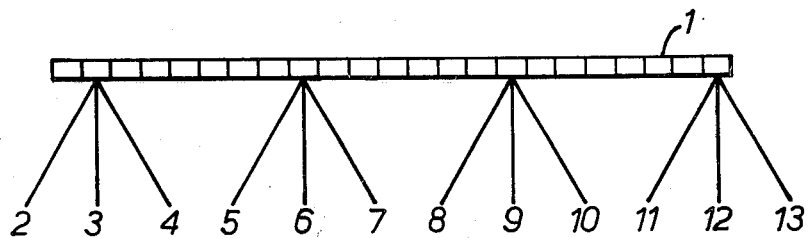
FIG. 2 shows a typical pattern of lines of sight to be generated to form a compound scan pattern in accordance with this invention.

FIG. 2 shows a compound scan pattern which has not previously been used in the ultrasonic examination of objects using a linear transducer array. In accordance with this pattern, a single echogram is formed by a first sector scan from a first group of elements 1, the scan being composed of a plurality of lines of sight of which lines 2, 3 and 4 are examples, and then another sector scan is formed from another group of elements 1 at a different position with lines 5, 6 and 7 as examples, and so on for a plurality of sector positions. As explained earlier, if such a pattern is to be used in the visualization of the heart with a resolution of 1 millimeter over an examination area of 10 centimeters square with a maximum depth below the surface of 15 centimeters, each line of sight requires at least 200$\mu$sec of time for its acquisition and thus if four sector scans are utilized each of 100 lines, the total scan pattern requires 80msec. The corresponding echogram repetition rate is therefore 12 frames per second which may give a reduced visual presentation due to flicker. This may be improved by reducing the number of sectors or reducing the number of lines per sector.

Figure 3:
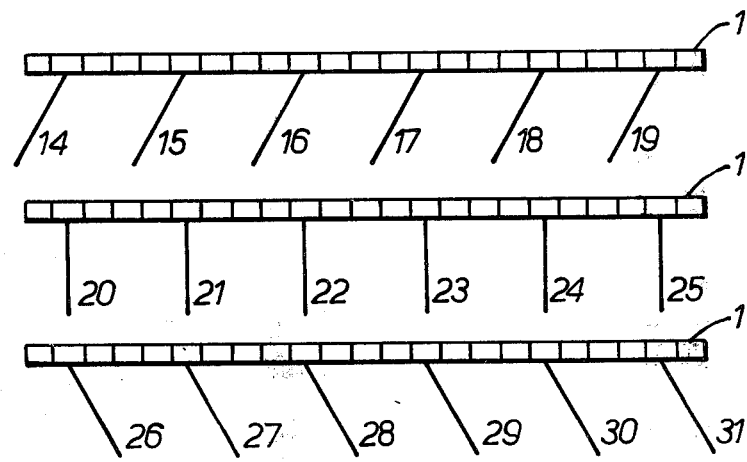
FIG. 3 shows an alternative method of producing a compound scan pattern in accordance with the invention.

To further increase te quality of the presentation a scanning pattern such as shown in FIG. 3 may be adopted. FIG. 3 shows a scan pattern in which all the scan lines 14, 15, . . . , 19 from different groups of elements 1 are at a constant angle and for instance there may be 100 such lines. This frame of information can be acquired in the example mentioned above, in 20 msecs. The next frame of information is then acquired from the groups of elements 1 consisting of a plurality of lines including 20, 21, . . . , 25 in a different direction, and the next succeeding frame consisting of lines 26, 27, . . . , 31 in yet another direction. In this way a compound scan echogram can be obtained with a high flicker rate by using the averaging properties of the eye to superimpose lines of sight in different directions on consecutive ultrasonic echogram frames.

Figure 4:
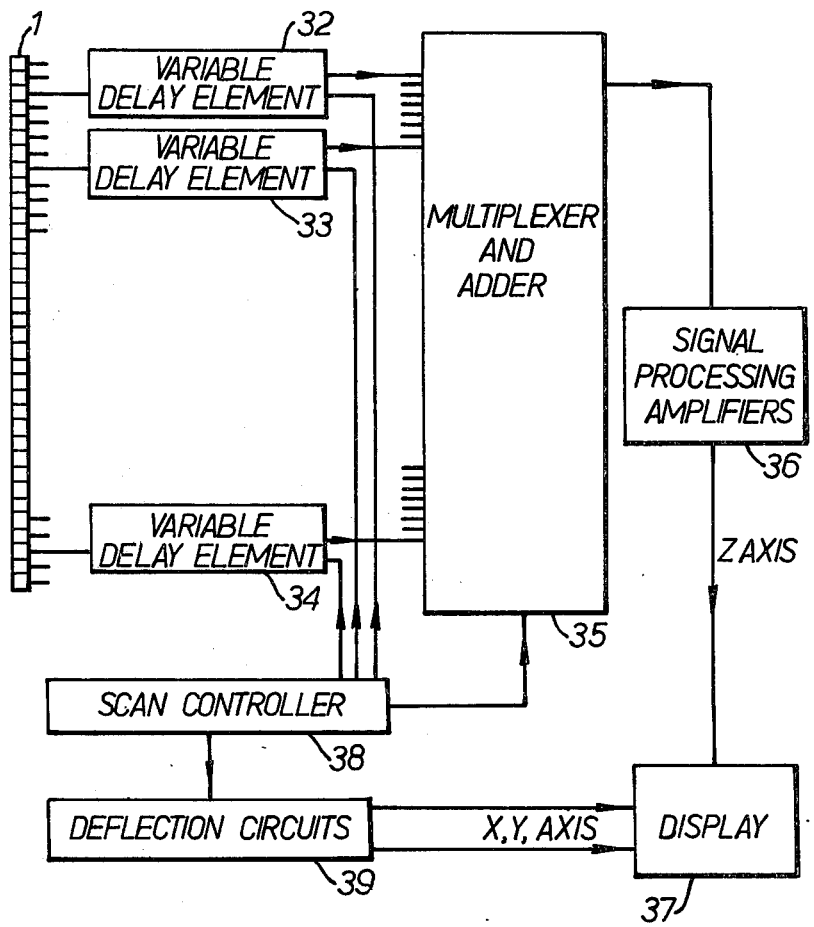
FIG. 4 shows a block diagram of the electronic apparatus which may be used to display the information obtained in accordance with this invention.

FIG. 4 shows a block diagram of an electronic system suitable for generating the scan patterns shown in FIG. 2 and FIG. 3. The individual elements in the figure are known, for example, from U.S. Pat. No. 3,166,731 to Joy and U.S. Pat. No. 3,086,195 to Halliday, and can be implemented in a number different ways using known electronic design techniques. In the figure, the array elements 1 are each connected to a variable delay element 32 and 34 and thence to a multiplexer and adder element 35. Using known techniques which vary the variable delay elements 32 to 34 and appropriately switching the multiplexer and adder 35 the beams shown in FIGS. 2 and 3 can be readily generated both on transmission and on reception. In addition, again using known techniques, the beams can be focussed at a fixed distance on transmission and on a variable distance which is varied throughout the reception time on reception. The output of the multiplexer and adder 35 can be considered as a standard ultrasonic echo signal such as would normally be obtained from a conventional transmitter/receiver transducer in the present systems. The signal processing amplifier 36 again is conventional and similar to those known and used in this art at present and its output provides the Z axis or intensity input of a standard CRT display 37. The scan controller 38 which may consist of a hard wired electronic logic circuit using conventional components or, in a preferred version, a general purpose digital mini computer controls the delay of each of the variable delay elements 32 to 34 and also controls the switching pattern of the multiplexer and adder 35. Similar control signals are provided to the deflection circuits 39 which generate lines on the display 37 which represent the position and direction of the beams in the scan patterns generated by the scan controller 38.

In another embodiment the scan controller may be used to direct a beam from a number of the transducer elements 1 to allow pulsed Doppler information to be obtained from a selected small region within the larger area scanned by the scan patterns shown in FIGS. 2 and 3. In this instance, the B mode echogram produced by display 37 is used as a frame of reference to ensure accurate positioning of the regions from which the Doppler signals are acquired. Measurement of blood flow may be effected by the technique described in U.S. Pat. No. 3,939,707.

While the present invention has been described herein with reference to preferred embodiments, it will be generally understood by those skilled in the art that various changes may be made and equivalents substituted for elements thereof without departing from the true spirit and scope of the invention.

I claim:

1. Apparatus for the ultrasonic examination of an object, comprising:
   a linear transducer array for transmitting pulses of ultrasonic energy into the object and receiving echoes of the pulses reflected by acoustic impedance discontinuities within the object, said transducer array including a plurality of adjacent transducer elements;
   means for energizing the elements of a group of said elements in a plurality of different sequences, each of said different sequences causing said group to cooperatively transmit a pulse of energy along a beam in a different one of a plurality of angular directions in a single plane; and
   means for activating different non-exclusive groups of adjacent transducer elements within said array in turn, so that each group directs pules of ultrasonic energy into the object and receives echoes reflected along beams in said plurality of angular directions.

2. Apparatus as claimed in claim 1 further including means to activate said linear transducer array to transmit pulses of ultrasonic energy into portion of said object along a beam in said plane and to determine the shift in frequency of echoes of said pulses caused by flow of liquid in said portion.

3. Apparatus for the ultrasonic examination of an object, comprising:
   a linear transducer array for directing pulses of ultrasonic energy into the object and receiving echoes of said pulses reflected by acoustic impedance discontinuities within the object, said transducer array including a plurality of adjacent transducer elements;
   means for energizing the elements in a group of said elements in a plurality of different sequences, each of said different sequences causing said group to cooperatively transmit a pulse of energy along a beam in a different one of a plurality angular directions in a single plane; and
   means for activating non-exclusive groups of adjacent transducer elements within said array so that each group sequentially directs pulses of ultrasonic energy into the object and receives echoes reflected along said plurality of angular directions.

4. Apparatus as claimed in claim 3 further including means to activate said linear transducer array to transmit pulses of ultrasonic energy into portion of said object along a beam in said plane and to determine the shift in frequency of echoes of said pulses caused by flow of liquid in said portion.

5. A method of ultrasonic examination of an object comprising the steps of:
   directing pulses of ultrasonic energy along a plurality of beams into said object; and
   receiving echoes of said pulses reflected along said beams by acoustic impedance discontinuities within said object, each of said pulses being directed and echoes received by one of a plurality of non-exclusive groups of adjacent transducer elements within a linear transducer array which includes a plurality of transducer elements, said pulses being directed in turn by each group along beams in a plurality of angular directions in a single plane by sequentially activating the elements in a group to cooperatively produce a single directed pulse.

6. A method of ultrasonic examination of an object comprising the steps of:
   directing pulses of ultrasonic energy along a plurality of beams into said object; and
   receiving echoes of said pulses reflected along said beams by acoustic impedance discontinuities within said object, each of said pulses being directed and echoes received by one of a plurality of non-exclusive groups of adjacent transducer elements within a linear transducer array which includes a plurality of transducer elements, said pulses being sequentially directed by said groups in each of a plurality of angular directions in a single plane by sequentially activating the elements in a group to cooperatively produce a single directed pulse.

* * * * *